(12) United States Patent
Buss et al.

(10) Patent No.: US 11,565,096 B2
(45) Date of Patent: Jan. 31, 2023

(54) DELIVERY SYSTEM FOR A PHARMACEUTICAL, HOLISTIC OR MEDICINAL COMPONENT

(71) Applicant: Herphoric, Inc., Paradise Valley, AZ (US)

(72) Inventors: Paul Buss, Paradise Valley, AZ (US); James Kinney, Cincinnati, OH (US)

(73) Assignee: Herphoric, Inc., Paradise Valley, AZ (US)

( * ) Notice: Subject to any disclaimer, the term of this patent is extended or adjusted under 35 U.S.C. 154(b) by 0 days.

(21) Appl. No.: 17/575,956

(22) Filed: Jan. 14, 2022

(65) Prior Publication Data
US 2022/0218967 A1 Jul. 14, 2022

Related U.S. Application Data

(60) Provisional application No. 63/137,252, filed on Jan. 14, 2021.

(51) Int. Cl.
*A61M 31/00* (2006.01)
(52) U.S. Cl.
CPC ... *A61M 31/002* (2013.01); *A61M 2202/0007* (2013.01); *A61M 2210/1475* (2013.01)
(58) Field of Classification Search
CPC .............. A61M 31/002; A61M 31/007; A61M 2202/0007; A61M 2210/1475; A61F 6/14; A61F 13/20; A61K 9/02; A61K 9/025
See application file for complete search history.

(56) References Cited

U.S. PATENT DOCUMENTS

| | | | |
|---|---|---|---|
| 2,509,241 | A | 5/1950 | Mende |
| 2,739,593 | A | 3/1956 | McLaughlin |
| 2,829,646 | A | 4/1958 | Kurkjian |
| 2,832,342 | A | 4/1958 | Leonora |

(Continued)

FOREIGN PATENT DOCUMENTS

| AU | 2003214813 B2 | 11/2007 |
|---|---|---|
| DE | 202011110360 U1 | 1/2014 |

(Continued)

OTHER PUBLICATIONS

Karki et al.; "Thin films as an emerging platform for drug delivery"; Asian Journal of Pharmaceutical Sciences II; Jun. 2016; p. 559-574.

(Continued)

*Primary Examiner* — Tasnim Mehjabin Ahmed
(74) *Attorney, Agent, or Firm* — BakerHostetler

(57) ABSTRACT

A tampon and delivery system for a pharmaceutical, holistic or medicinal component, includes: (1) a nonabsorbent vaginal implant having a generally cylindrical shape including a leading end and a cylindrical outer surface; (2) an outer delivery sheath applied to at least a portion of the cylindrical outer surface of the tampon, distal from the leading end (and preferably leaving the leading end exposed), where the outer delivery sheath comprises a formulation including (a) a water soluble polymer film carrier and (b) a pharmaceutical, holistic or medicinal component; and (3) an applicator containing the tampon and applied delivery sheath. Methods for preparation of the delivery system and methods of use are also disclosed.

29 Claims, 3 Drawing Sheets

(56) References Cited

U.S. PATENT DOCUMENTS

| | | |
|---|---|---|
| 3,515,138 A | 6/1970 | Hochstrasser et al. |
| 3,656,483 A | 4/1972 | Rudel |
| 3,731,682 A | 5/1973 | Fielding |
| 3,884,233 A | 5/1975 | Summey |
| 3,902,493 A | 9/1975 | Baier et al. |
| 3,916,898 A | 11/1975 | Robinson |
| 3,918,452 A | 11/1975 | Cornfeld |
| 3,921,636 A | 11/1975 | Zaffaroni |
| 4,186,742 A | 2/1980 | Donald |
| 4,286,596 A | 9/1981 | Rubinstein |
| 4,308,867 A * | 1/1982 | Roseman ............ A61F 13/2074 424/431 |
| 4,317,447 A | 3/1982 | Williams |
| 4,318,405 A | 3/1982 | Sneider |
| 4,424,054 A | 1/1984 | Conn et al. |
| 4,536,178 A | 8/1985 | Lichstein et al. |
| 5,437,628 A | 8/1995 | Fox et al. |
| 5,468,236 A | 11/1995 | Everhart et al. |
| 6,086,909 A | 7/2000 | Harrison et al. |
| 6,315,763 B1 | 11/2001 | Albright et al. |
| 6,359,191 B1 | 3/2002 | Rusch et al. |
| 6,416,779 B1 | 7/2002 | Augustine et al. |
| 6,558,352 B1 | 5/2003 | Chaffringeon |
| 6,572,874 B1 | 6/2003 | Harrison et al. |
| 6,691,704 B2 | 2/2004 | Bini et al. |
| 6,712,784 B2 | 3/2004 | Huang |
| D492,033 S | 6/2004 | Jarmon et al. |
| 6,758,840 B2 | 7/2004 | Knox |
| 6,888,043 B2 | 5/2005 | Geiser et al. |
| 6,899,700 B2 | 5/2005 | Gehling et al. |
| 7,144,391 B1 * | 12/2006 | Kreutz .................. A61F 13/515 604/385.18 |
| 7,815,928 B2 * | 10/2010 | Cherif Cheikh ..... A61K 9/0024 424/426 |
| 9,155,872 B2 | 10/2015 | Kumar et al. |
| 10,799,399 B1 | 10/2020 | Whack |
| 11,083,635 B2 | 8/2021 | Pendleton et al. |
| 2003/0040727 A1 | 2/2003 | Boulanger et al. |
| 2003/0153864 A1 | 8/2003 | Chaffringeon |
| 2003/0233077 A1 | 12/2003 | Swick |
| 2003/0233078 A1 | 12/2003 | Swick |
| 2004/0077924 A1 | 4/2004 | Zunker et al. |
| 2004/0078013 A1 | 4/2004 | Zunker et al. |
| 2004/0199100 A1 | 10/2004 | Lemay et al. |
| 2004/0249352 A1 | 12/2004 | Swick |
| 2005/0037072 A1 | 2/2005 | Pather et al. |
| 2005/0070839 A1 | 3/2005 | Jackson et al. |
| 2005/0244402 A1 | 11/2005 | Villanueva et al. |
| 2005/0256482 A1 | 11/2005 | Minoguchi et al. |
| 2006/0100566 A1 | 5/2006 | Zbella et al. |
| 2006/0213918 A1 | 9/2006 | Rajala et al. |
| 2006/0213919 A1 | 9/2006 | Heuer et al. |
| 2006/0216334 A1 | 9/2006 | Gehling et al. |
| 2006/0217652 A1 | 9/2006 | Heuer et al. |
| 2006/0247571 A1 | 11/2006 | Hayes et al. |
| 2007/0027096 A1 | 2/2007 | Chen et al. |
| 2007/0129668 A1 | 6/2007 | Swick |
| 2007/0141118 A1 | 6/2007 | Damico et al. |
| 2007/0156077 A1 | 7/2007 | Pfister |
| 2007/0219479 A1 | 9/2007 | Tasbas |
| 2012/0071839 A1* | 3/2012 | Wada .................. A61F 13/2074 604/286 |
| 2012/0238993 A1* | 9/2012 | Nazzaro .................. A61L 27/54 604/59 |
| 2013/0345678 A1 | 12/2013 | Rubin |
| 2016/0120708 A1 | 5/2016 | Chaffringeon |
| 2017/0056635 A1* | 3/2017 | Dimino .................. A61P 43/00 |
| 2019/0282513 A1 | 9/2019 | Yerike |
| 2020/0163807 A1* | 5/2020 | Tumey ................. A61K 9/0036 |
| 2020/0323699 A1 | 10/2020 | Buss |

FOREIGN PATENT DOCUMENTS

| | | | |
|---|---|---|---|
| EP | 0988009 A1 | 3/2000 | |
| EP | 1322252 B1 * | 7/2006 | ......... A61F 13/2051 |
| EP | 2298259 A2 | 3/2011 | |
| FR | 2853226 A1 | 10/2004 | |
| TW | I623304 B | 5/2018 | |
| WO | WO 2001/052785 A1 | 7/2001 | |
| WO | WO 2003/020240 A2 | 3/2003 | |
| WO | WO 2003/059318 A2 | 7/2003 | |
| WO | WO 2003/063829 A1 | 8/2003 | |
| WO | WO 2004/087026 A1 | 10/2004 | |

OTHER PUBLICATIONS

Bala et al.; "Orally dissolving strips: A new approach to oral drug delivery system"; Int'l Journal of Pharmaceutical Investigation; vol. 3 Issue 2; Apr. 2013; p. 67-76.

International Patent Application No. PCT/US2020/067621; Int'l Written Opinion and Search Report; dated May 3, 2021; 11 pages.

* cited by examiner

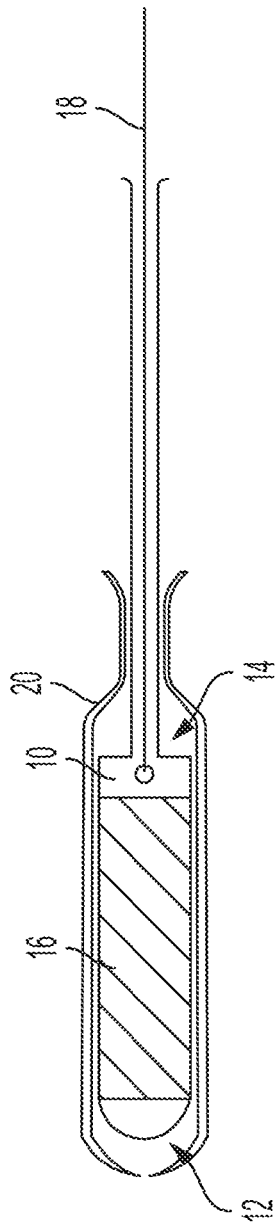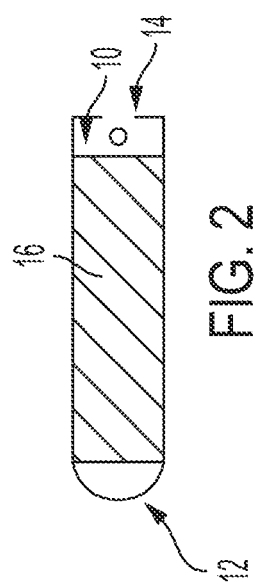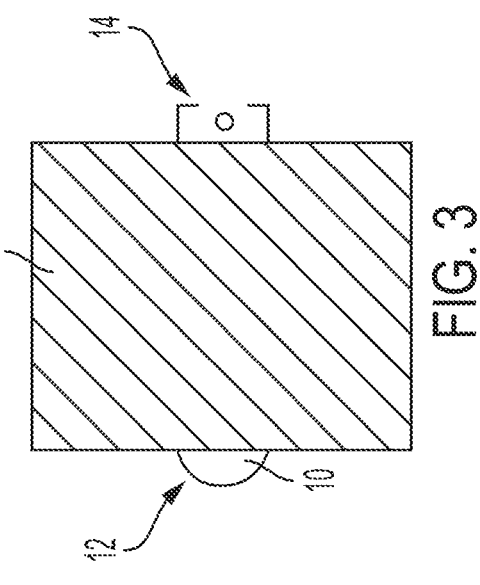

DELIVERY SYSTEM FOR A PHARMACEUTICAL, HOLISTIC OR MEDICINAL COMPONENT

CROSS REFERENCE TO RELATED APPLICATIONS

The current application claims the benefit of U.S. Provisional Application No. 63/137,252, filed Jan. 14, 2021; the entire enclosure of which is incorporated herein by reference.

BACKGROUND

In modern medicine, a primary goal in the administration of medication is to deliver such medication to the body of the individual by the most direct route to the target of the medication. In other words, delivery of a drug to treat a medical ailment of a patient should be highly targeted to reach and treat the ailment for which the medication is intended in the least amount of time, with the least amount of communication of the medication administered to areas of the body not requiring it. Such accurate targeting is especially desired where other parts of the body may react adversely to the medication, or where a circuitous route through the body may dilute the medication.

In the case of vaginal disorders which may occur monthly such as menstrual pain, which in studies impacts up to 80% of women and up to 10% with debilitating symptoms that limit normal daily routine, or which may be caused by viruses, yeast, or other pathogens, it is desirable that a treating medication be delivered directly to the vaginal cavity of the person. Further, in some cases, it is desirable that the medication delivery be prolonged so as to have time to communicate to regions of the vaginal canal, cervix, or uterus without problems from body fluids draining from the delivery area preventing medication delivery.

Multiple delivery systems have been employed over recent decades to provide such targeted and prolonged delivery. However, because of issues with drug delivery via the vaginal canal, suppositories and foams which provide carriers for the medication frequently fail or are rendered less than effective due to fluid flow and drainage from the canal. Tampon related devices, while advantageous for ease of use and familiarity to the user, have been tried, but the prior art is configured in such a manner that the released medication can actually be absorbed by the tampon rather than delivered to the body of the user. Furthermore, the use of a tampon as part of the delivery mechanism limits the useable window of time and the population of women that can benefit from using the device without potential adverse impact. Using an absorbent device such as a tampon outside of menses can lead to residual fiber loss, that can be breeding grounds for viruses, yeast, or other pathogens, as well as create micro tears in the vaginal epithelium which can allow for the spread of those pathogens into the bloodstream, one example of this can result in TSS (Toxic Shock Syndrome).

The forgoing prior art examples concerning vaginal drug delivery are intended to be illustrative and not exclusive, and they do not imply any limitations on the invention described and claimed herein. Various other limitations of the related art are known or will become apparent to those skilled in the art upon a reading and understanding of the specification below and the accompanying drawings.

SUMMARY

The device and method herein provide a solution to the targeted delivery of medications to areas within or in direct communication with the vagina. Further, the system herein is employable for targeted delivery of medication, over a prolonged time period, through direct communication through the tissue of the vaginal canal to treat ailments directly, and to also communicate medications and the like to the bloodstream and surrounding areas.

Present disclosure relates to a device for vaginal drug delivery taking inspiration from a tried-and-true medical device, the tampon, evolving the device into a delivery solution that offers localized relief for women suffering from menstrual pain, endometriosis and other ailments, while expanding the usage beyond the typical population able to safely use the device. Further, the system herein is employable for targeted delivery of medication, over a prolonged time period or at a solubility rate that matches absorption of the target therapeutic, through direct communication through the tissue of the vaginal canal to treat ailments directly, and to also communicate medications and the like to the bloodstream and surrounding areas.

According to aspects of the current disclosure, the device and delivery system for a therapeutic agent (pharmaceutical, holistic or medicinal component), includes: a non-absorbent vaginal implant component having a generally cylindrical shape including a curved and tapered leading end and a cylindrical outer surface; an outer delivery sheath applied to at least a portion of the cylindrical outer surface of the implant, distal from the leading end, the outer delivery sheath including (a) a water-soluble polymer film carrier and (b) a therapeutic agent; and an applicator containing the apparatus and applied polymer film. An alternate configuration of the device could include a fixed or removably engaged dissolvable capsule located at the leading end of the implant in place of or in conjunction with the outer delivery sheath. So positioned, the device delivers a therapeutic agent or combination of therapeutics in the right place at the right time. The therapeutic agent does not pass through the digestive system. The woman does not have to change her habits to deliver the product.

With respect to the above description, before explaining at least one preferred embodiment of the herein disclosed vaginal drug delivery system invention in detail, it is to be understood that the invention is not limited in its application to the details of construction and to the arrangement of the components in the following description or illustrated in the drawings. The invention herein described and shown is capable of other embodiments and of being practiced and carried out in various other ways by those skilled in the art upon reading this disclosure. Also, it is to be understood that the phraseology and terminology employed herein are for the purpose of description and should not be regarded as limiting.

As such, those skilled in the art will appreciate that the conception upon which this disclosure is based may readily be utilized as a basis for designing of other vaginal drug delivery devices and for carrying out the several purposes of the present disclosed device. It is important, therefore, that the claims be regarded as including such equivalent construction and methodology insofar as they do not depart from the spirit and scope of the present invention.

In one embodiment for the treatment of pain, such as caused by dysmenorrhea, the use of an analgesic as the therapeutic agent, more specifically a nonsteroidal anti-inflammatory (NSAID) such as Ibuprofen, is preferred. In a similar embodiment the therapeutic agent is a botanically derived species such as a cannabinoid, more specifically Cannabidiol (CBD) or Cannabidiolic Acid (CBDA), some studies, in addition to the pain-relieving anti-inflammatory effects of cannabinoids, have identified potential antiemetic, anxiolytics effects among other benefits being studied. In another embodiment, for the treatment of an unbalanced vaginal microbiome leading to the risk of infection, the use of a probiotic as the therapeutic agent such as a *Lactobacillus* species, more specifically *L. crispatus*, is used.

In a more detailed embodiment, the therapeutic agent component is up to 50% of the outer delivery sheath. Alternately, or in addition, the outer delivery sheath is formulated so as to adhere to vaginal wall. Alternately, or in addition, the outer delivery sheath includes about 1 to 200 mg of the therapeutic agent. Alternately, or in addition, the delivery sheath is about 1 mil to 20 mil in thickness.

In one embodiment, the device may be provided as a capsule adapted for engagement to, or provided in combination with, a cylindrical vaginal implant component, which may or may not also include a dissolvable outer delivery sheath. The capsule may be a dissolvable polymer such as PCL or other material, which is impregnated with, and/or has a cavity therein, which holds the medications to be delivered to the targeted area via the vaginal canal. In a similar embodiment of the device herein, the capsule and cylindrical outer delivery sheath can be formed as a unitary structure. In this mode the capsule may dissolve at a concurrent rate as the dissolution of the outer delivery sheath, or it could dissolve more rapidly. In another embodiment of the device herein, the capsule may be configured in the same dissolvable manner so as to provide ongoing delivery of medication locally. However, the dissolvable capsule may be adapted for a removable engagement to a reusable apparatus. In use, the capsule, in this configuration, will disengage and dissolve over time. Such will allow for the capsules bearing the medication required for the patient to be dispensed from a pharmacy and engaged to the device whereupon they would release on insertion and dissolve over time.

It is an object of the present disclosure to provide an easily employed vaginal drug delivery system and method therefor.

These and other objects, features, and advantages of the present vaginal drug delivery device and method in the system herein, as well as the advantages thereof over existing prior art, which will become apparent from the description to follow, are accomplished by the improvements described in this specification and hereinafter described in the following detailed description which fully discloses the invention, but should not be considered as placing limitations thereon in any fashion.

BRIEF DESCRIPTION OF DRAWING FIGURES

The accompanying drawings, which are incorporated herein and form a part of the specification, illustrate some, but not the only or exclusive examples of embodiments and/or features of the disclosed system employing the device and method herein. It is intended that the embodiments and figures disclosed herein are to be considered illustrative of the invention herein, rather than limiting in any fashion.

In the drawings:

FIG. 1 is a side view of a pharmaceutical, holistic or medicinal delivery mechanism according to an embodiment of the current disclosure, provided on a nonabsorbent vaginal implant and positioned in an applicator component where the applicator component is shown in cross-section;

FIG. 2 is a side view of an exemplary pharmaceutical, holistic or medicinal delivery mechanism provided on a nonabsorbent vaginal implant, without the applicator component and the removal component;

FIG. 3 is a side view of an exemplary pharmaceutical, holistic or medicinal delivery mechanism prior to being installed about a circumference of a nonabsorbent vaginal implant;

DETAILED DESCRIPTION

Figure 4:
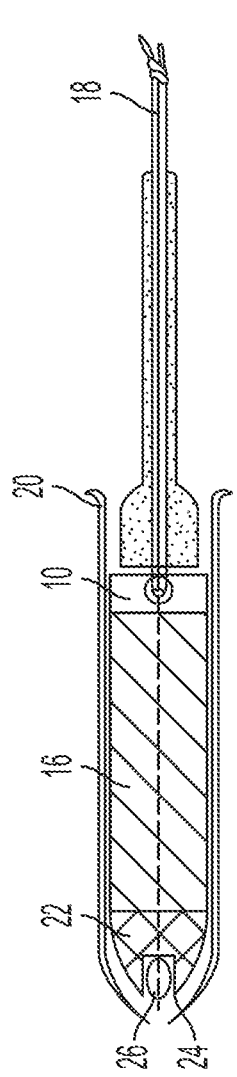
FIG. 4 is a cross-section view of an alternate embodiment of the pharmaceutical, holistic or medicinal delivery mechanism, including an additional tip delivery component.

Referring to FIGS. 1-3, the current disclosure is directed to a delivery system for a pharmaceutical, holistic or medicinal component (the current disclosure is also directed to methods for constructing such a delivery system and the current disclosure is also directed to methods for using such a delivery system). The system includes a nonabsorbent vaginal implant 10 having a generally cylindrical shape including a tapered and curved leading end 12, a distal end 14 and a generally cylindrical outer surface. In an embodiment, the nonabsorbent implant 10 is generally in the shape of a tampon but does not have the absorbing properties of the tampon. Preferably, the vaginal implant is a temporary implant (removable using a string 18, for example). The system also includes an outer delivery sheath 16 applied about a portion of the outer cylindrical surface of the implant 10, distal from the leading end (i.e., the distal end is substantially free from the outer delivery sheath). The outer delivery sheath 16 includes a water-soluble polymer film carrier that carries a pharmaceutical, holistic or medicinal component. The implant 10 may also include a conventional tampon string 18 extending from the distal end and a conventional tampon applicator assembly 20 containing the implant 10 and outer delivery sheath 16. In an embodiment, the implant 10 may be reusable.

The nonabsorbent implant 10 may be constructed of any material, or combination of materials, known for surgical or non-surgical insertion or implantation into a human body. In an embodiment, the implant 10 is solid, hollow cylinder constructed of such material(s).

In an embodiment, the water-soluble polymer film is formulated with the pharmaceutical, holistic or medicinal component before applying to the cylindrical outer surface of the implant. Such a water-soluble polymer film may be commercially available from a company called ARx, product identification ARCare 93488 non-tacky dissolvable film.

In an embodiment, the pharmaceutical, holistic or medicinal component includes CBD. In a more detailed embodiment, the CBD component may take up to 50 percent of the outer delivery sheath. For example, the outer delivery sheath may include 100 milligrams of material, where the CBD takes up to 50 milligrams of the delivery sheath material.

In an embodiment, the sheath 16 formulation contains Ibuprofen at ~50% concentration. In a more detailed embodiment, the sheath 16 is ~11 mil thick, 40 mm×50 mm solid film, comprised primarily of a combination of natural polymers as discussed herein with a sugar alcohol based plasticizer and a nonionic surfactant.

In an embodiment, the outer delivery sheath 16 is in the form of a sheet (e.g., cut from a web) applied about a portion of the cylindrical outer surface of the implant 10. The outer delivery sheath may be formulated so as to adhere to the vaginal wall within the vaginal canal. In an embodiment, the outer delivery sheath 16 is about 5 to about 6 millimeters distal from the leading end 12. In an embodiment, the outer delivery sheath 16 includes about 1 to about 100 milligrams of the pharmaceutical, holistic or medicinal component. In an embodiment, the delivery sheath 16 is about 1 mil to about 4 mil in thickness.

In use, when the implant 10 and delivery sheath 16 is inserted into the patient's vaginal canal, the formulation of the delivery sheath 16 allows for the delivery sheath to adhere to the patient's vaginal wall which allows for more effective and quick transfer of the pharmaceutical, holistic or medicinal component into the patient's bloodstream. Further, if the pharmaceutical, holistic or medicinal component is CBD, for example, the current device allows the delivery to the bloodstream of the CBD component in the area of menstrual cramps more effectively and quickly.

The formulation of the outer delivery sheath is designed to safely dissolve in the patient's body over time. Testing has shown that embodiments of the outer delivery sheath 16 effectively and completely dissolve in less than 30 minutes.

An embodiment of the device can be manufactured by first, formulating the water-soluble polymer film with an effective amount of the pharmaceutical, holistic or medicinal component. Then the formulation is cured/hardened in the form of a web of flexible material (sufficiently flexible so that it can be rolled about a tampon and fastened together as a sheath) that is typically between 1 mil to 4 mil in thickness, but may be as thick as up to 20 mil. Next, the web is cut into multiple rectangular tabs 16' as shown in FIG. 3, each of which may be separately wrapped around an outer circumferential surface of the nonabsorbent implant 10. Once the tab 16' is wrapped around the outer circumferential surface of the implant 10, it forms a sheath 16. In an embodiment, the film of the sheath 16 is adhered to itself around the implant 10. This can be done via heat, a small amount of moisture and/or by using an adhesive. In an embodiment, the sheath 16 is not directly adhered to the implant 10, rather the sheath 16 is attached to itself about the implant 10 tight enough to stay in place on the implant surface while being inserted. Once inserted, in the presence of vaginal fluids the sheath 16 will separate from the implant and break apart.

Once the sheath 16 is applied about the outer circumferential surface of the tampon-shaped implant 10, the implant 10 and sheath 16 may then be installed into a conventional tampon applicator device 20.

The thickness of the outer delivery sheath 16 may be varied during manufacture to control the rate that the delivery sheath dissolves; thereby controlling the rate of delivery of the pharmaceutical, holistic or medicinal component to the patient. In one exemplary formulation of the change in thickness exhibited a linear relationship to the dissolution time for an oral test. A 47% reduction in film thickness had on average a 44% reduction in dissolution time. Dissolution time may be also affected by the polymer composition, concentration of the therapeutic, the presence of additives (plasticizers, cellulosics, etc.), moisture uptake in the film and pH.

The disclosed delivery system is effective because it may use conventional tampon applicators so that the patient will have comfort and practice using the delivery device.

The device provides an axially positioned cylindrical sheath 16 encompassing the implant's cylindrical outer surface area that can be composed of materials that deliver targeted benefits to the user at a desired solubility rate activated by the vaginal fluids and conditions such as temperature and pH.

In this description, the directional prepositions of up, upwardly, down, downwardly, front, back, top, upper, bottom, lower, left, right and other such terms refer to the device as it is oriented and appears in the drawings and are used for convenience only and such are not intended to be limiting or to imply that the device has to be used or positioned in any particular orientation. Additionally, where the word substantially is used, such is intended to be plus or minus twenty percent, unless otherwise defined upon such use.

Figure 5:
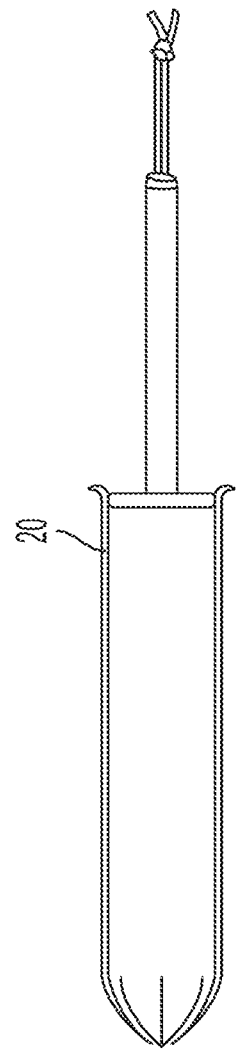
FIG. 5 is a side view of the embodiment of FIG. 4.

Now referring to drawings in FIGS. 4-9, wherein similar components are identified by like reference numerals, there is seen in FIGS. 4 and 5 a mode in which a separate tip 22 is engaged to the distal end of the cylindrical nonabsorbent implant 10.

In the mode of the device of FIGS. 4 and 5, the tip 22 is formed of a fluid-dissolvable material such as PCL. The material of the tip 22 may be the same as that of the sheath 16 but may also be a different material that has different dissolving properties as discussed herein. The dissolvable material forming one or both of the tip 22 and the sheath 16 may be impregnated with the desired therapeutic agent or agents to be delivered to the vaginal canal during the dissolving of the tip 22 and the sheath 16.

The tip 22 may be formed in a solid solution of dissolvable polymer as described herein or other material which is impregnated with the therapeutic agent, or it may be formed with a slot 24 extending into the leading end of the tip 22 which is surrounded by walls forming the tip 22. Where the slot 24 is provided, dissolvable medication 26 may be positioned within the slot 24.

In an embodiment, the tip 22 may itself be a capsule that contains medication (not shown) within an enclosed cavity (not shown) contained in the tip 22. In this embodiment the therapeutic will disperse into the vaginal canal once an opening forms in the wall of the tip 22 as the tip dissolves, exposing the enclosed cavity.

Figure 9:
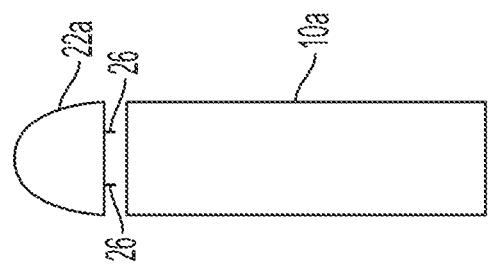
FIG. 9 is an exploded view of FIG. 8.

As depicted in FIG. 9, the implant 10a may be formed with an engageable tip 22a, which is adapted to engage with a distal end of implant 10a. This mode allows for doctors and pharmacies to stock multiple medications which are preferably delivered through the vaginal cavity. As can be discerned, tips 22a having an infinite number of different medications may be stocked and provided which treat specific patient ailments and may be engaged to a stock cylindrical implant 10a. This allows for high customability of the capsules 22a which are impregnated with one or a plurality of medications which dissolve as the capsule dissolves.

Figure 6:
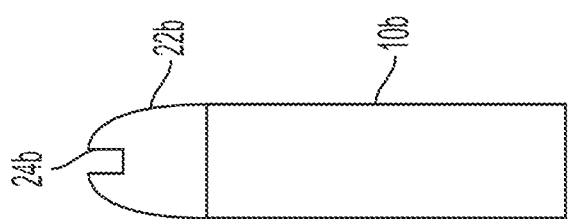
FIG. 6 is a side view of an alternate embodiment incorporating an alternate tip delivery component.
Figure 7:
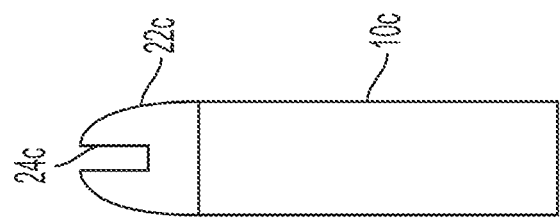
FIG. 7 is a side view of an alternate embodiment incorporating another alternate tip delivery component.
Figure 8:
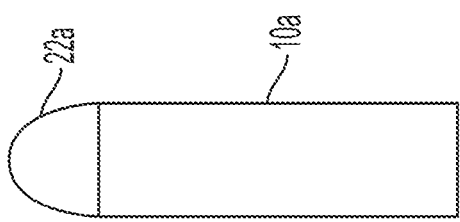
FIG. 8 is a side view of an alternate embodiment incorporating another alternate tip delivery component.

Referring to FIGS. 6 and 7, capsules 22b or 22c having a secondary supply of one or a plurality of medications may be provided where the tip 22b or 22c is formed with a tip slot 24b or 24c. This secondary medication supply may be pre-positioned within the tip slot 24b or 24c, or for example, may be positioned in the enclosed cavity (in the embodiment in which the tip itself is a capsule) by a medical professional using, for example, a hypodermic needle which is temporarily communicated through the wall of the tip 22 surrounding the enclosed cavity.

In an embodiment, the removably engageable dissolving tip 22 may be configured with mating connectors 26 or adhesive, which is configured to engage on or with the distal end of the cylindrical implant 10. Such, for example, connectors 26 might be pins or hooks or other projections which engage with complementary connectors positioned on leading/distal end of the cylindrical implant housing 10.

In an embodiment, the dissolving tip 22 may be adapted for an engagement with a medication such as the depicted tablet, caplet or capsule 26. In this mode, the tablet 26 of medication or supplement of choice shown is positioned within the tip slot 24 in the dissolvable tip 22 which is adapted to engage it. Such might be, for example, by forming the sidewalls of the tip slot 24 to be flexible and forming the width of the slot smaller than most conventionally available tablets and capsules 26 used for medications and supplements. In use, the tablet or capsule 26 is slid into a compressive engagement within the slot 24 such as shown in FIG. 6. The medication and/or supplement provided in the capsule 26 will thus be delivered to the vaginal canal where it can dissolve.

The current disclosure envisions many possible options for the pharmaceutical, holistic or medicinal component (also referred to herein as the therapeutic agent or the API) in the delivery sheath. The current disclosure briefly discusses each of the following groups (pharmaceutical, medical, and holistic) and provides examples of each group that may be included in the polymer film.

The pharmaceuticals group includes a potential list of ingredients. Depending on the application, one pharmaceutical ingredient may be preferred over another (e.g., based on the condition being treated). However, any of the following pharmaceuticals could be added to the polymer solution. The pharmaceuticals may be used appropriately in the polymer solution, independently or in combination, based on FDA approved medical research for the "relief" of or proven "cure" for certain diseases and ailments. The pharmaceuticals group may include one, or a combination of two or more of the following:

1. Antipyretics
2. Analgesics
3. Antimalarials
4. Antibiotics
5. Mood Stabilizers
6. Hormone Replacements
7. Stimulants
8. Tranquilizers
9. Statins
10. Antacids
11. Reflux Suppressants
12. Antiflatulents
13. Antidopaminergics
14. Proton Pump Inhibitors (PPIS)
15. Hz-Receptor Antagonists
16. Cytoprotectants
17. Prostaglandin Analogues
18. Laxatives
19. Antispasmodics
20. Antidiarrhoeals
21. Bile Acid Sequestrants
22. Opioids
23. B-Receptor Blockers ("Beta Blockers")
24. Calcium Channel Blockers
25. Diuretics
26. Cardiac Glycosides
27. Antiarrhythmics
28. Nitrates
29. Antianginals
30. Vasoconstrictors
31. Vasodilators
32. ACE Inhibitors
33. Angiotensin Receptor Blockers
34. Beta-Blockers
35. A Blockers
36. Thiazide Diuretics
37. Loop Diuretics
38. Aldosterone Inhibitors
39. Coagulation
40. Anticoagulants
41. Heparin
42. Antiplatelet Drugs
43. Fibrinolytics
44. Anti-Hemophilic Factors
45. Haemostatic Drugs
46. HMG-Coa Reductase Inhibitors
47. Hypolipidaemic Agents
48. Anaesthetics
49. Antipsychotics
50. Antidepressants (Including Tricyclic Antidepressants, Monoamine Oxidase Inhibitors, Lithium Salts, And Selective Serotonin Reuptake Inhibitors (SSRIS))
51. Antiemetics
52. Anticonvulsants/Antiepileptics
53. Anxiolytics
54. Barbiturates
55. Movement Disorder (E.G., Parkinson's Disease) Drugs
56. Stimulants (Including Amphetamines)
57. Benzodiazepines
58. Cyclopyrrolones
59. Dopamine Antagonists
60. Antihistamines
61. Cannabinoids
62. 5-HT (Serotonin) Antagonists
63. Analgesic Drugs
64. Nsaids (Including COX-2 Selective Inhibitors)
65. Muscle Relaxants
66. Neuromuscular Drugs
67. Anticholinesterases
68. Bronchodilators
69. Antitussives
70. Mucolytics
71. Decongestants
72. Corticosteroids
73. Beta2-Adrenergic Agonists
74. Anticholinergics
75. Mast Cell Stabilizers
76. Leukotriene Antagonists
77. Androgens
78. Antiandrogens
79. Estrogens
80. Gonadotropin
81. Corticosteroids
82. Human Growth Hormone
83. Insulin
84. Antidiabetics (Sulfonylureas, Biguanides/Metformin, Thiazolidinediones, Insulin)
85. Thyroid Hormones, A
86. Ntithyroid Drugs
87. Calcitonin
88. Diphosponate
89. Vasopressin Analogues
90. Alkalinizing Agents
91. Quinolones
92. Cholinergics
93. Antispasmodics
94. 5-Alpha Reductase Inhibitor
95. Selective Alpha-1 Blockers, 96. Sildenafils
97. Fertility Medications
98. Hormonal Contraception
99. Ormeloxifene
100. Haemostatic Drugs
101. Antifibrinolytics
102. Hormone Replacement Therapy (HRT)
103. Bone Regulators
104. Beta-Receptor Agonists
105. Follicle Stimulating Hormone
106. Luteinising Hormone
107. LHRH
108. Gamolenic Acid
109. Gonadotropin Release Inhibitor
110. Progestogen
111. Dopamine Agonists
112. Oestrogen
113. Prostaglandins
114. Gonadorelin
115. Clomiphene
116. Tamoxifen
117. Diethylstilbestrol
118. Antifungals
119. Antileprotics
120. Antituberculous Drugs
121. Antimalarials
122. Anthelmintics
123. Amoebicides
124. Antivirals
125. Antiprotozoals
126. Probiotics
127. Prebiotics
128. Vaccines
129. Immunoglobulins
130. Immunosuppressants
131. Interferons
132. Monoclonal Antibodies
133. Anti-Allergies
134. Antihistamines
135. Corticosteroids
136. Electrolytes
137. Mineral Preparations (Including Iron Preparations And Magnesium Preparations)
138. Parenteral Nutritions
139. Vitamins
140. Anti-Obesity Drugs
141. Anabolic Drugs
142. Haematopoietic Drugs
143. Food Product Drugs
144. Cytotoxic Drugs
145. Therapeutic Antibodies
146. Sex Hormones
147. Aromatase Inhibitors
148. Somatostatin Inhibitors
149. Recombinant Interleukins
150. G-CSF
151. Erythropoietin While there are thousands of different drugs, all marketed drugs fall under one or more tiers of the American Hospital Formulary Service (AHFS) Pharmacologic-Therapeutic Classification System. This classification was developed and is maintained by the American Society of Health-System Pharmacists (ASHP), a national association of pharmacists. The classification includes the following groups of medicines:

1. Antihistamine Drugs (including the prescription drugs Clarinex and Xyzal and OTC medicines Allegra, Benadryl, Claritin, Chlor-Trimeton, Dimetane, Zyrtec and Tavist)
2. Anti-infective Agents (including penicillins and antivirals)
3. Antineoplastic Agents
4. Autonomic Drugs
5. Blood Derivatives
6. Blood Formation, Coagulation, and Thrombosis Agents
7. Cardiovascular Drugs (including digoxin, acebutolol, propranolol and lisinopril)
8. Cellular Therapy
9. Central Nervous System (CNS) Agents (including stimulants and depressants)
10. Contraceptives
11. Dental Agents
12. Diagnostic
13. Electrolytic, Caloric, and Water Balance
14. Enzymes
15. Respiratory Tract Agents
16. Eye, Ear, Nose, and Throat (EENT) Preparations
17. Gastrointestinal Drugs (including rabeprazole sodium, nitazoxanide, bevacizumab and nizatidine)
18. Gold Compounds
19. Heavy Metal Antagonists
20. Hormones and Synthetic Substitutes
21. Local Anesthetics
22. Oxytocics
23. Radioactive Agents
24. Serums, Toxoids, and Vaccines
25. Skin and Mucous Membrane Agents
26. Smooth Muscle Relaxants (including cyclobenzaprine and carisoprodol)
27. Vitamins
28. Miscellaneous Therapeutic Agents
29. Pharmaceutical Aids The holistic group includes a potential list of ingredients, several of which are listed below. The holistic group may include herbal, vitamin, and/or mineral (single or in combination) additives as a remedy for disease and/or pain (mental, physical, or emotional), or discomfort by way of tinctures; essential oils; plant, flower or root extracts; cell salts; sarcodes; nosodes; and vitamins, to name a few. The holistic group may include ingredients used in naturopathic medicine, traditional Chinese and Eastern medicines, and Ayurvedic medicine. This category may also include non-vitamin supplements, such as fish oil, Omega-3 fatty acid, glucosamine, chondroitin, or flaxseed oil. The holistic group may include one or more of the following ingredients:

1. *Ginkgo biloba*
2. *Hypericum perforatum*
3. Herbal pollen extract NOS
4. *Senna alexandrina*
5. Herbal extract NOS
6. *Cimicifuga racemosa*
7. *Echinacea purpurea*
8. *Plantago ovata*
9. *Serenoa repens*
10. *Glycine max*
11. *Oenothera biennis*
12. *Vitis vinifera*
13. *Cannabis sativa*
14. *Cannabis indica*
15. *Mentha* x *piperita*
16. *Citrus* x *paradisi*
17. *Valeriana officinalis*

18. *Silybum marianum*
19. *Viscum album*
20. *Allium sativum*
21. *Vitex agnus-castus*
22. *Pelargonium reniforme* root
23. *Digitalis purpurea*
24. *Ginseng* NOS
25. Humic acid
26. Vitamin A, B-6, B-12, C, D, E, K
27. Chromium
28. Folic acid
29. Calcium
30. Iron
31. Zinc
32. Plant, Fruit and Nut tinctures, concentrates or extracts In an embodiment, the water-soluble polymer film 16 and/or the dissolvable tip 22 is preferentially formulated using a combination of natural polymers such as pullulan, sodium alginate, maltodextrin, gelatin, or starch. Combining two or more of which can allow the formulator the flexibility to balance between several important properties such as solubility in water, viscosity, mucoadhesion, swelling, film formation, and mechanical properties. These properties can be further enhanced with the use of plasticizers and small quantities of surfactants. However, this should not limit the use of synthetic polymers, such as HPMC, CMC, HPC, PCL, PVA, PVP, or PEO, which one or more, or in combination with the natural polymers offer a range of benefits and could be particularly useful to overcome the compatibility challenges or short comings with various therapeutic agents and their impacts on the film properties.

A representative formula can fall within the following composition ranges on a weight basis, but should not be limiting due to the unique needs of a particular therapeutic agent:

| | |
|---|---|
| Therapeutic Agent(s) | ~5-50% |
| Water Soluble Polymer(s) | ~30-70% |
| Plasticizer(s) | ~0-20% |
| Surfactant(s) | ~0-5% |
| Filler(s) | ~0-5% |

The following Table 1 is a non-exhaustive list of possible polymers for use with exemplary formulations, along with information about each of the polymer's properties and key findings.

TABLE 1

| Polymer | Type | Mw range | $H_2O$ Solubility | Mucoadhesion | Swelling | Key Comments |
|---|---|---|---|---|---|---|
| Pullulan | Natural | 8,000-2,000,000 | High | High | Moderate | Can benefit from blending with other polymers |
| Sodium Alginate | Natural | 10,000-600,000 | High | High | High | High compatibility with other polymers |
| Pectin | Natural | 30,000-100,000 | High | High | High | Forms brittle film |
| Gelatin | Natural | 15,000-250,000 | Temperature dependent | Low - Moderate | High | Temperature dependent properties |
| Hydroxypropyl methylcellulose (HPMC) | Synthetic | 10,000-1,500,000 | Moderate | Moderate | Moderate | Can assist in delayed release properties |
| Carboxymethyl cellulose (CMC) | Synthetic | 90,000-700,000 | High | High | High | Good in combination with alginates |
| Poly (vinyl pyrrolidone) (PVP) | Synthetic | 2,500-3,000,000 | Moderate | High | High | Best properties when blended with other polymers |
| Poly (vinyl alcohol) (PVA) | Synthetic | 20,000-200,000 | High | Moderate | High | Forms very flexible film |

This Table 1 is based upon information found the following article: Karki, et. al., *Thin Films as an Emerging Platform for Drug Delivery* (Asian Journal of Pharmaceutical Sciences, June 2016). Another informative article is Bala, et. al., *Orally Dissolving Strips: A New Approach to Oral Drug Delivery System* (Int J Pharm Investig April-June 2013). Each of these articles are incorporated herein by reference.

The type, proportion, and chemical nature of plasticizers may affect the film formation from polymeric aqueous dispersions and as result, the final properties of the film. Indeed, polyols such as polyethylene glycol (PEG), diethylene glycol (DEG), glycerol (GLY), xylitol, sorbitol, fructose, and sucrose are considered as effective plasticizers to improve some properties of biopolymer films.

Surfactants or surface active agents can be used to aid in dispersing, wetting, solubilizing, and emulsifying to enable a more homogenous mixture or solution. This is especially important when using otherwise incompatible ingredients such as the use of a lipophilic therapeutic in a hydrophilic polymer system. The proper selection of which can result in a more stable film and can aid in the dissolution in an aqueous media as well as to aid in the overall absorption of the therapeutic agent. Typical surfactants used can include sodium laurel sulfate, benzalkonium chloride, polyoxymethylene stearates, poloxamers, as well as Tween, and Span type products among others.

Fillers is a more generic category which can include a range of additives in low concentrations. These can include additives for aesthetic purposes such as colorants like TiO2 or be used for rheology modification of the liquid film during manufacturing or as a stabilizing agent in the solid film. This can include a range of cellulosics or natural gums such as xanthan gum, locust bean gum, or carrageenan.

Mucoadhesive properties of the delivery sheath 16 may arise from the polymer component as shown above in Table 1.

Certain embodiments of the current disclosure may utilize multiple layers in the composition of the film 16. For example, an exemplary film 16 may include a radially inner layer and a radially outer layer, where the radially outer layer that is in initial contact with the mucosa is formulated to dissolve faster than the radially inner layer. Such a radially outer layer may provide a larger dose of the therapeutic for quicker initial relief with a lower dose of the therapeutic in the slower dissolving radially inner layer 16a for a long term relief. As another example, one of the layers may include a first therapeutic agent while the other layer may include a second therapeutic agent. The first therapeutic agent may be formulated/selected to have a more local effect while the second therapeutic agent may be formulated/selected to have a more systemic uptake. As another example, the radially inner layer may be formulated as a slower-dissolving protective layer that protects the more quickly dissolving outer layer from being absorbed into the tampon prior to diffusion through the epithelial layers. As another example, the inner layer may be used more as a nonabsorbent (or substantially slower absorbing) adhesive or barrier layer that does not include a therapeutic agent. Such a nonabsorbent inner layer may allow the outer layer to have a slower dissolution time, which may be an option for a longer release mechanism. As another example, the outer layer may be formulated to give additional mechanical properties to the sheath in the case that the therapeutic agent in the inner layer is difficult to incorporate or requires a formulation that lacks certain properties need for manufacturing or storage/distribution.

Various formulation adjustments can be made between the different layers to change the dissolution properties. This can be done though polymer selection by utilizing the inherent properties of a chemical structure or by modifying the molecular weight or polydispersity, as an example increasing the molecular weight of a polymer can have positive benefits on mechanical properties, but often leads to a decrease in solubility in part due to an increases in chain entanglement. Alternatively, this can also be adjusted via the use of other additives such as plasticizers or surfactants. Increasing plasticizer content often has a negative impact of solubility, while surfactants can be used to increase the wetting/swelling properties of the polymer which can aid in solubility.

Examples of a localized therapeutic agent could be a probiotic such as a *Lactobacillus* species or mixture to balance the vaginal microbiome or an antibiotic such as Metronidazole or Clindamycin for the treatment of bacterial vaginosis. Examples of a therapeutic which can exhibit a systemic mode of action could include analgesics or cannabinoids.

Selection of different formulations for the sheath 16 versus the tip 22 may also be provided in much the same way as described above for selections of different layers of the sheath.

What is claimed is:

1. A delivery system for a pharmaceutical, holistic or medicinal component, comprising:
   a nonabsorbent solid and hollow vaginal implant having a generally cylindrical shape including a leading end and a cylindrical outer surface; and
   an outer layer applied to at least a portion of the cylindrical outer surface of the implant, the outer layer including (a) a water soluble polymer film carrier and (b) a pharmaceutical, holistic or medicinal component.

2. The delivery system of claim 1, wherein the pharmaceutical, holistic or medicinal component includes CBD.

3. The delivery system of claim 2, wherein the CBD component is up to 50% of the outer layer.

4. The delivery system of claim 1, wherein the implant is a temporary implant.

5. The delivery system of claim 1, wherein the outer layer is a sheath comprised of a flexible sheet of delivery layer material wrapped about the cylindrical outer surface of the implant and attached to itself.

6. The delivery system of claim 5, wherein the sheath is not directly adhered to the implant.

7. The delivery system of claim 5, wherein the sheath is designed to break apart in the presence of vaginal fluids.

8. The delivery system of claim 5, wherein the sheath is formulated so as to adhere to vaginal wall.

9. The delivery system of claim 1, wherein the outer layer is positioned about 5 to 6 mm distal from the leading end.

10. The delivery system of claim 1 wherein the outer layer includes about 1 to 100 mg of the pharmaceutical, holistic or medicinal component.

11. The delivery system of claim 1, wherein the outer layer is about 1 mil to 4 mil in thickness.

12. The delivery system of claim 1, further comprising a dissolvable tip provided on the leading end of the implant.

13. The delivery system of claim 12, wherein the dissolvable tip is formulated from a second formulation comprising (c) a water-soluble polymer film carrier and (d) a pharmaceutical, holistic or medicinal component.

14. The delivery system of claim 12, wherein the dissolvable tip includes a chamber or slot containing a therapeutic.

15. The delivery system of claim 12, wherein the dissolvable tip is a capsule containing a therapeutic therewithin.

16. The delivery system of claim 12 wherein the dissolvable tip is integrated with the outer layer.

17. A delivery system for a pharmaceutical, holistic or medicinal component, comprising:
   a nonabsorbent vaginal implant having a generally cylindrical shape including a leading end and a cylindrical outer surface;
   an outer delivery sheath applied to at least a portion of the cylindrical outer surface of the implant, the outer delivery sheath including a first inner radial layer and a second outer radial layer, wherein at least one of the first or second radial layers is comprised of (a) a water soluble polymer film carrier and (b) a pharmaceutical, holistic or medicinal component; and
   an applicator containing the implant and the applied outer delivery sheath;
   wherein the first inner radial layer is comprised of (a) a first water soluble polymer film carrier and (b) a first pharmaceutical, holistic or medicinal component, and the second outer radial layer is comprised of (c) a second water soluble polymer film carrier and (d) a second pharmaceutical, holistic or medicinal component, wherein the second outer radial layer is formulated to dissolve more quickly than the first inner radial layer.

18. A delivery system of for a pharmaceutical, holistic or medicinal component, comprising:
a nonabsorbent vaginal implant having a generally cylindrical shape including a leading end and a cylindrical outer surface;
an outer delivery sheath applied to at least a portion of the cylindrical outer surface of the implant, the outer delivery sheath including a first inner radial layer and a second outer radial layer, wherein at least one of the first or second radial layers is comprised of (a) a water soluble polymer film carrier and (b) a pharmaceutical, holistic or medicinal component; and
an applicator containing the implant and the applied outer delivery sheath;
wherein the second outer radial layer comprises a larger dose of the pharmaceutical, holistic or medicinal component as compared to the first inner radial layer.

19. A delivery system of for a pharmaceutical, holistic or medicinal component, comprising:
a nonabsorbent vaginal implant having a generally cylindrical shape including a leading end and a cylindrical outer surface;
an outer delivery sheath applied to at least a portion of the cylindrical outer surface of the implant, the outer delivery sheath including a first inner radial layer and a second outer radial layer, wherein at least one of the first or second radial layers is comprised of (a) a water soluble polymer film carrier and (b) a pharmaceutical, holistic or medicinal component; and
an applicator containing the implant and the applied outer delivery sheath;
wherein the first inner radial layer is comprised of (a) a first water soluble polymer film carrier and (b) a first pharmaceutical, holistic or medicinal component, and the second outer radial layer is comprised of (c) a second water soluble polymer film carrier and (d) a second pharmaceutical, holistic or medicinal component, wherein the first and second pharmaceutical, holistic or medicinal components are different for each of the first and second radial layers.

20. The delivery system of claim 19, wherein the second pharmaceutical, holistic or medicinal component of the second outer radial layer is formulated to have a more localized effect as compared to the first pharmaceutical, holistic or medicinal component, and the first pharmaceutical, holistic or medicinal component of the first inner radial layer is formulated to have a more systemic effect as compared to the second pharmaceutical, holistic or medicinal component.

21. A method for constructing a delivery system for a pharmaceutical, holistic or medicinal component, comprising the steps of:
providing a nonabsorbent vaginal implant having a generally cylindrical shape including a leading end and a cylindrical outer surface;
applying an outer delivery sheath to at least a portion of the cylindrical outer surface of the implant, the outer delivery sheath including (a) a water-soluble polymer film carrier and (b) a pharmaceutical, holistic or medicinal component; and
installing the implant and applied outer delivery sheath into an applicator;
wherein the applying step includes the following steps:
providing a web of flexible material including (a) the water-soluble polymer film carrier and (b) the pharmaceutical, holistic or medicinal component;
cutting a rectangular tab from the flexible web; and
wrapping the rectangular tab about the cylindrical outer surface of the implant.

22. The method of claim 21, wherein the applying step further comprises adhering opposing ends of the rectangular tab to each other after the wrapping step.

23. The method of claim 21, wherein the sheath includes two layers, at least one of the two layers including (a) the water-soluble polymer film carrier and (b) the pharmaceutical, holistic or medicinal component.

24. The method of claim 21, wherein the applying step positions the sheath about 5 to 6 mm distal from the leading end.

25. A delivery system for a pharmaceutical, holistic or medicinal component, comprising:
a nonabsorbent solid and hollow vaginal implant having a generally cylindrical shape including a leading end and a cylindrical outer surface; and
a dissolvable tip provided on the leading end of the implant, the tip carrying a pharmaceutical, holistic or medicinal component.

26. The delivery system of claim 25, wherein the dissolvable tip is formulated from a formulation comprising (a) a water-soluble polymer film carrier and (b) the pharmaceutical, holistic or medicinal component.

27. The delivery system of claim 25, wherein the dissolvable tip includes a chamber or slot containing the pharmaceutical, holistic or medicinal component.

28. The delivery system of claim 25, wherein the dissolvable tip is a capsule containing the pharmaceutical, holistic or medicinal component therewithin.

29. The delivery system of claim 25, wherein the dissolvable tip is integrated with a sheath formulated from (a) a water soluble polymer film carrier and (b) the pharmaceutical, holistic or medicinal component, wherein the sheath surrounds at least a portion of the cylindrical outer surface of the implant.

* * * * *